US012616764B2

(12) United States Patent
Yagyu

(10) Patent No.: US 12,616,764 B2
(45) Date of Patent: May 5, 2026

(54) INACTIVATING DEVICE AND OPTICAL FILTER

(71) Applicant: Ushio Denki Kabushiki Kaisha, Tokyo (JP)

(72) Inventor: Hideaki Yagyu, Tokyo (JP)

(73) Assignee: Ushio Denki Kabushiki Kaisha, Tokyo (JP)

(\*) Notice: Subject to any disclaimer, the term of this patent is extended or adjusted under 35 U.S.C. 154(b) by 499 days.

(21) Appl. No.: 18/055,187

(22) Filed: Nov. 14, 2022

(65) Prior Publication Data

US 2023/0293743 A1     Sep. 21, 2023

(30) Foreign Application Priority Data

Nov. 18, 2021     (JP) ................................. 2021-187813

(51) Int. Cl.
| | |
|---|---|
| *A61L 2/26* | (2006.01) |
| *A61L 2/10* | (2006.01) |
| *G02B 5/20* | (2006.01) |

(52) U.S. Cl.
CPC ....... *A61L 2/10* (2013.01); *A61L 2/26* (2013.01); *G02B 5/208* (2013.01); *A61L 2202/11* (2013.01)

(58) Field of Classification Search
None
See application file for complete search history.

(56) References Cited

U.S. PATENT DOCUMENTS

| | | | |
|---|---|---|---|
| 2018/0311386 A1* | 11/2018 | Hawkins | ................... F21V 7/00 |
| 2019/0192708 A1 | 6/2019 | Igarashi | |

| | | | |
|---|---|---|---|
| 2019/0192709 A1 | 6/2019 | Igarashi | |
| 2019/0321499 A1* | 10/2019 | Igarashi | ................... A61L 2/26 |
| 2022/0068627 A1 | 3/2022 | Yagyu et al. | |
| 2022/0409755 A1 | 12/2022 | Yagyu | |

(Continued)

FOREIGN PATENT DOCUMENTS

| | | | |
|---|---|---|---|
| JP | 6025756 B2 | 11/2016 | |
| JP | 2019-115525 A | 7/2019 | |
| JP | 6947261 B1 | 10/2021 | |

(Continued)

OTHER PUBLICATIONS

The extended European search report issued by the European Patent Office on Apr. 18, 2023, which corresponds to European Patent Application No. 22206664.9-1020 and is related to U.S. Appl. No. 18/055,187.

(Continued)

*Primary Examiner* — James Choi
(74) *Attorney, Agent, or Firm* — Studebaker Brackett PLLC

(57) ABSTRACT

An inactivating device includes: an ultraviolet light source to emit ultraviolet light, a main light-emission wavelength band of the ultraviolet light being at least partly included in a range from 200 nm to 230 nm inclusive; and an optical filter including a multilayer dielectric film, wherein with respect to the ultraviolet light incident at an incidence angle of 0 degrees, the optical filter has a band in which the ultraviolet light in a range of wavelengths from 190 nm to 235 nm inclusive is transmitted, and a wavelength λ5 at which transmittance of the optical filter indicates 5% is longer than or equal to 236 nm and shorter than 245 nm.

7 Claims, 9 Drawing Sheets

(56)  References Cited

U.S. PATENT DOCUMENTS

| 2023/0041901 | A1* | 2/2023 | Baxter | A61L 2/10 |
| 2023/0305204 | A1* | 9/2023 | Imamura | G02B 5/208 |

FOREIGN PATENT DOCUMENTS

| JP | 2023-042316 A | 3/2023 |
| WO | 2012/122210 A1 | 9/2012 |
| WO | 2021/043554 A1 | 3/2021 |

OTHER PUBLICATIONS

Sachiko Kaidzu et al.; "Re-Evaluation of Rat Corneal Damage by Short-Wavelength UV Revealed Extremely Less Hazardous Property of Far-UV-C+"; Photochemistry and Photobiology; 2021; 97: 505-516.

Communication pursuant to Article 94(3) EPC issued by the European Patent Office on Dec. 23, 2024, which corresponds to European Patent Application No. 22 206 664.9-1001 and is related to U.S. Appl. No. 18/055,187.

"Notice of Reasons for Refusal" Office Action issued in JP 2021-187813; mailed by the Japanese Patent Office on Feb. 4, 2025.

An Office Action; "Notice of Reasons for Refusal," mailed by the Japanese Patent Office on Jun. 27, 2025, which corresponds to Japanese Patent Application No. 2021-187813 and is related to U.S. Appl. No. 18/055,187; with English language translation.

* cited by examiner

1

20

10

Z
X ← → Y

1

10

30b

30b

20

30

30a

X

Z → Y

1

30

INACTIVATING DEVICE AND OPTICAL FILTER

CROSS-REFERENCE TO RELATED APPLICATION

The present invention claims the benefit of priority to Japanese Patent Application No. 2021-187813 filed on Nov. 18, 2021 with the Japanese Patent Office, the entire contents of which are incorporated herein by reference in its entirety.

BACKGROUND OF THE INVENTION

Field of the Invention

The present invention relates to an inactivating device for bacteria or viruses and particularly to a device for inactivating bacteria or viruses using ultraviolet light. The present invention also relates to an optical filter used in a device for inactivating bacteria or viruses using ultraviolet light.

Description of the Related Art

Technologies for inactivating bacteria or viruses by irradiating them with ultraviolet light have been known. Since DNA exhibits the highest absorption characteristics around a light wavelength of 260 nm, ultraviolet light with wavelengths around 254 nm emitted from light sources such as low-pressure mercury lamp is used in many cases. Methods for inactivating bacteria or viruses by ultraviolet light are characterized by being able to sterilize a target space or a target object only by irradiating the target space or the target object with ultraviolet light without spraying with chemicals or the like.

It is known that ultraviolet light in a wavelength band has high risk of affecting the human body and ultraviolet light in another wavelength band has low risk of affecting the human body. Thus, in recent years, methods or devices for inactivating bacteria or viruses present in a room by ultraviolet light in a wavelength band with low risk of affecting the human body have been considered. For instance, Patent Document 1 shown below gives a description of a sterilizing device (an inactivating device) that uses ultraviolet light in a wavelength range of 190 nm to 230 nm, which has an extremely small influence on the human body.

Prior Art Document

Patent Document
Patent Document 1: JP-B-6025756

Non-Patent Document

Non-Patent Document 1: Sachiko Kaidzu et al. "Re-Evaluation of Rat Corneal Damage by Short-Wavelength UV Revealed Extremely Less Hazardous Property of Far-UV-C†" Photochemistry and Photobiology, 2021, 97: 505-516

SUMMARY OF THE INVENTION

It is an object of the present invention to provide an improved inactivating device by suppressing an increase in intensity of ultraviolet light in a wavelength band that affects the human body while increasing intensity of the ultraviolet light in a wavelength band that has a small influence on the human body.

An inactivating device according to the present invention includes:

an ultraviolet light source to emit ultraviolet light, a main light-emission wavelength band of the ultraviolet light being at least partly included in a range from 200 nm to 230 nm inclusive; and an optical filter including a multilayer dielectric film, wherein with respect to the ultraviolet light incident at an incidence angle of 0 degrees, the optical filter has a band in which the ultraviolet light in a range of wavelengths from 190 nm to 235 nm inclusive is transmitted, and a wavelength $\lambda 5$ at which transmittance of the optical filter indicates 5% is longer than or equal to 236 nm and shorter than 245 nm.

In the present specification, "inactivation" refers to a concept that includes killing bacteria or viruses and weakening infectivity or toxicity. And "bacteria" refer to microorganisms such as bacteria and fungi (molds). The "bacteria or viruses" may be hereinafter collectively referred to as "pathogens".

In the present specification, a "main light-emission wavelength band" refers to a wavelength band across which an intensity spectrum of light emitted from a light source shows a light intensity higher than or equal to 10% of a peak intensity of the intensity spectrum. For the ultraviolet light source described above, a peak wavelength of the ultraviolet light is preferably within a range from 190 nm to 235 nm and is more preferably within a range from 210 nm to 235 nm.

In recent years, the influence of ultraviolet light on the human body has been researched and verified in a progressive manner. It is proved that ultraviolet light is apt to be absorbed in a skin surface layer and ectocornea and is characterized as improving in safety with a decrease in wavelength. In particular, it is proved that ultraviolet light with a wavelength of shorter than 240 nm has low risk of affecting the human body. It is proved that ultraviolet light with a wavelength of shorter than or equal to 230 nm has extremely low risk of affecting the human body. For instance, Non-Patent Document 1 above gives a report about results obtained by verification of the generation of cyclobutane pyrimidine dimers (CPD), which is DNA damage induced by radiation of ultraviolet light and is a factor in the incidence of cancer.

According to Non-Patent Document 1, ultraviolet light of wavelengths 207 nm and 222 nm ultraviolet light, when irradiated to the cornea of an organism, only reach the top layer of the corneal epithelium. Therefore, CPD occurs only in the uppermost layer of the corneal epithelium. CPDs generated in the top layer of the corneal epithelium are usually detached from the cornea within 24 hours during the physiological turnover cycle, so very few CPDs remain on the cornea.

In recent years, many reports have been made concerning the verification of influence of ultraviolet light (particularly ultraviolet light with wavelengths of 200 nm to 230 nm) on the human body as described above. Inactivating devices using ultraviolet light in a wavelength band with a small influence on the human body, in particular, have recently attracted attention partly due to the recent coronavirus (COVID-19) pandemic.

Such inactivating devices are expected to produce the effect of inhibiting contact infection passed via an object surface and infection passed via atmospheric aerosol while using ultraviolet light in a wavelength band with an extremely small influence on the human body. Hence, the feasibility of installing such an inactivating device in a space where people are frequently coming and going or in a room where people work for many hours has been studied.

However, although ultraviolet light with wavelengths of 190 nm to 230 nm has an extremely small influence on the human body compared to ultraviolet light emitted from low-pressure mercury lamps, regulation values concerning an integrated irradiation dose to the human body are prescribed in consideration of safety. At the time of applying the present specification for a patent, it is recommended to set the integrated irradiation dose of ultraviolet light radiated to the human body to be less than or equal to the regulation value (a threshold limit value) defined by the American Conference of Governmental Industrial Hygienists (ACGIH). For instance, the threshold limit value for the integrated irradiation dose of ultraviolet light with a wavelength of 222 nm a day (eight hours) is specified to be 22 mJ/cm$^2$. In the present specification, the threshold limit value is a current numerical value and is a numerical value that may be altered in the future. In addition to the above case, it is desirable to specify a predetermined upper limit value for the integrated irradiation dose of any ultraviolet light radiated to the human body from a safe operation perspective.

As a result, an inactivating device that is expected to irradiate a room, such as a space where people are coming and going, with ultraviolet light is required to be able to efficiently inactivate bacteria or viruses in a treatment target room or on a treatment target object while adhering to the regulation value for the integrated irradiation dose of the ultraviolet light described above.

Non-Patent Document 1 above gives a report about results obtained by verification of threshold values for the integrated irradiation dose at which a corneal disorder is caused by ultraviolet light with wavelengths of 207 nm and 222 nm. Non-Patent Document 1 reported that the threshold values for the integrated irradiation dose at which a corneal disorder by radiation of the ultraviolet light was observed were 10,000 mJ/cm$^2$ to 15,000 mJ/cm$^2$ for the ultraviolet light with a wavelength of 207 nm and 3,500 mJ/cm$^2$ to 5,000 mJ/cm$^2$ for the ultraviolet light with a wavelength of 222 nm. The values shown by the results are extremely high values as compared to regulation values prescribed by ACGIH at the present point in time. Since a large number of such verification results have been announced, current regulation values concerning the integrated irradiation dose of ultraviolet light in a specific wavelength band are expected to be revised.

If the regulation value of the integrated irradiation dose is increased, inactivation devices using ultraviolet light are expected to be used in such ways as irradiating ultraviolet light at higher intensities or turning the lights on constantly in spaces where people come and go, in order to more efficiently inactivate the space or object to be treated.

However, if optical output of an ultraviolet light source is simply increased to boost irradiance of the ultraviolet light, the intensity of the ultraviolet light in a wavelength band affecting the human body increases, and there is concern about heightened risk of health damage caused by irradiation of the human body with such ultraviolet light. In other words, as described above, in order to respond to a situation in which the regulation values for the integrated irradiation dose are increased in the future, ways and means are required to enable the inactivating device using ultraviolet light to increase only the intensity of the ultraviolet light in a wavelength band with a small influence on the human body without increasing the intensity of the ultraviolet light in a wavelength band affecting the human body.

If the ultraviolet light of the inactivating device is always lit in a space where people are coming and going, there is a possibility that a person may be irradiated with the ultraviolet light emitted from the device for a long time and the integrated irradiation dose of the ultraviolet light in a wavelength band with a substantial influence on the human body may increase. This causes concern about the risk of health damage.

Consequently, it is predicted that an inactivating device designed to emit ultraviolet light is required to increase intensity of the ultraviolet light in a wavelength band that has a small influence on the human body and concurrently suppress an increase in intensity of the ultraviolet light in a wavelength band that affects the human body more than ever in the future.

Next, even when a peak wavelength of ultraviolet light emitted from an ultraviolet light source belongs to a wavelength band with a small influence on the human body, a bottom part of an emission spectrum is present. Thus, there is a case in which a component of the light in a wavelength band affecting the human body is inevitably included. Hence, an inactivating device using ultraviolet light is generally provided with an optical filter to obstruct the ultraviolet light in a wavelength band affecting the human body, as in the sterilizing device (an inactivating device) described in Patent Document 1.

In view of conventional design philosophies, the optical filter is designed to display a satisfactorily high transmittance value in a wavelength band in which light is desired to be transmitted and a satisfactorily low transmittance value in a wavelength band in which the light is desired to be obstructed.

Meanwhile, in a wavelength band in a vicinity of a boundary between a wavelength band in which the light is desired to be transmitted and a wavelength band in which the light is desired to be obstructed, a wavelength at which the transmittance is 5% is, in some cases, called "wavelength $\lambda 5$" or "$\lambda 5$", etc. (hereinafter referred to as a "wavelength $\lambda 5$"). The "wavelength $\lambda 5$" and "$\lambda 5$" are sometimes used as an indicator when a characteristic parameter of a glass or a similar light-transmissive member or a device such as an optical filter used to obstruct light in a predetermined wavelength band is taken into consideration. In the present specification, the "wavelength $\lambda 5$" is associated with a wavelength defined based on a spectrum of ultraviolet light incident at an incidence angle of 0 degrees on a principal surface of a light transmissive window on which the optical filter is formed, unless otherwise specified.

A known optical filter through which ultraviolet light in a predetermined wavelength band is transmitted is an optical filter made from a multilayer dielectric film, for example. The optical filter formed by a multilayer dielectric film is characterized by an ability to adjust a wavelength band of the ultraviolet light in which the light is obstructed (conversely, a wavelength band of the ultraviolet light in which the light is transmitted) by changing a thickness of each layer.

The optical filter formed by a multilayer dielectric film has angle dependence and thus is characterized as being able to change characteristics, such as a peak value of the transmittance and a wavelength band in which the light is transmitted, in response to an incidence angle of the ultraviolet light. In this respect, a description is given later with reference to FIGS. 6 and 8.

Accordingly, in regard to an inactivating device using ultraviolet light, the inventor of the present invention reviewed a configuration with an incidence angle character-istic of an optical filter being taken into consideration.

First, the present inventor conducted verification of ultra-violet light emitted from an inactivating device under pre-determined conditions to ascertain how the incidence angle characteristic of an optical filter contributes to a ratio of an integrated dose of intensities of the ultraviolet light in a band of wavelengths from 235 nm to 320 nm inclusive, which includes a wavelength range with a potential influence on the human body, to an integrated dose of intensities of the ultraviolet light in a band of wavelengths from 200 nm to 230 nm inclusive with an extremely small influence on the human body (the ratio defined as a "harmful light ratio"). Details of the verification will be described later in the "DETAILED DESCRIPTION OF THE PREFERRED EMBODIMENTS" section.

According to results of the verification described above, ultraviolet light emitted from an inactivating device that includes an optical filter designed such that the wavelength $\lambda 5$ is 240 nm shows a harmful light ratio lower than that presented by ultraviolet light emitted from an inactivating device that includes an optical filter designed such that the wavelength $\lambda 5$ is 235 nm. A reason guessed for this is that out of angle components of radiant flux of the ultraviolet light generated by the ultraviolet light source and incident on the optical filter, components of the angles greater than 0 degrees play a responsible role.

The present inventor also considered harmful light ratios by incidence angle, based on results of the verification described above. For the optical filter designed such that the wavelength $\lambda 5$ is 240 nm, the harmful light ratio of the optical filter by incidence angle is less than or equal to 5% at an incidence angle ranging from 0 degrees to 50 degrees inclusive. In other words, it is observed that the optical filter designed such that the wavelength $\lambda 5$ is 240 nm has a high effect on reduction of the harmful light ratio particularly for the light incident at the incidence angle in the angle range.

The harmful light ratio of the optical filter designed such that the wavelength $\lambda 5$ is longer than or equal to 236 nm and shorter than 245 nm is less than or equal to 30% at an incidence angle ranging from 0 degrees to 50 degrees. The characteristic of the optical filter described here will be described later in the "DETAILED DESCRIPTION OF THE PREFERRED EMBODIMENTS" section with refer-ence to FIG. 10.

In other words, from the viewpoint of facilitating trans-mission of safe ultraviolet light without causing the harmful light ratio of the ultraviolet light to deteriorate, it is prefer-able to use an optical filter that is formed by a multilayer dielectric film such that the wavelength $\lambda 5$ is longer than or equal to 236 nm and shorter than 245 nm as described above. Moreover, it could be preferred that as for the light intensity of radiant flux in a relative intensity distribution of the incident ultraviolet light, the intensity of the ultraviolet light outside a range of the incidence angle from 10 degrees to 50 degrees inclusive is lower than the intensity of the ultraviolet light in the same incidence angle range. In other words, it is preferred that the relative intensity distribution shows an intensity peak at an incidence angle in a range from 10 degrees to 50 degrees inclusive.

Thus, preferably in the inactivating device, in a distribu-tion of a relative intensity for each angle component of radiant flux of the ultraviolet light generated by the ultra-violet light source and incident on the optical filter, the incidence angle at which the relative intensity shows a peak value is included in a range from 10 degrees to 50 degrees inclusive.

As observed from FIG. 10, the optical filter formed by the multilayer dielectric film reduces the harmful light ratio to less than or equal to 5% when the incidence angle is in a range of 10 degrees to 45 degrees inclusive and reduces the harmful light ratio to less than or equal to 3% when the incidence angle is in a range of 20 degrees to 40 degrees inclusive. Hence, the incidence angle at which the intensity shows a peak in the relative intensity distribution is more preferably within a range from 10 degrees to 45 degrees inclusive and is particularly preferably within a range from 20 degrees to 40 degrees inclusive.

With the configuration described above, it is possible to achieve an inactivating device that suppresses an increase, as compared with conventional devices, in intensity of ultra-violet light in a wavelength band that affects the human body while increasing intensity of the ultraviolet light in a wave-length band that has a small influence on the human body.

A target product of the inactivating device of the present invention can provide sterilization and virus inactivation performance intrinsic to ultraviolet light without causing erythema or keratitis on the skin and eye of a human and an animal. In particular, unlike conventional low-pressure mer-cury lamps, the target product can be installed in an envi-ronment where people are present indoors and outdoors by taking advantage of the characteristic of the inactivating device of being able to be used in such an environment to irradiate the entire environment and provide virus inhibition and bacteria elimination in the air and on a surface of parts installed in the environment.

This accords with Goal 3 "Ensure healthy lives and promote well-being for all at all ages" included in sustain-able development goals (SDGs) led by the United Nations and will contribute greatly to the goal target 3.3 "By 2030, end the epidemics of AIDS, tuberculosis, malaria and neglected tropical diseases and combat hepatitis, water-borne diseases and other communicable diseases".

The inactivating device may include:
a housing that houses the ultraviolet light source; and
a light transmissive window to extract the ultraviolet light out of the housing,
wherein the optical filter is disposed on a principal surface of the light transmissive window.
In the inactivating device,
the optical filter may be configured such that the wave-length $\lambda 5$ is longer than or equal to 238 nm and shorter than 243 nm.
In the inactivating device,
the optical filter may include a member that includes a material to absorb the ultraviolet light in a wavelength range of shorter than or equal to 200 nm.
In the inactivating device,
the ultraviolet light source may be an excimer lamp that includes a light-emitting tube in which a gas containing krypton (Kr) and chlorine (Cl) as a light-emitting gas is sealed.

The excimer lamp, which includes the light-emitting tube in which a gas containing krypton (Kr) and chlorine (Cl) as a light-emitting gas is sealed, is a light source designed to emit ultraviolet light that has a peak wavelength of 222 nm and a main light-emission wavelength band included in a range from 200 nm to 230 nm inclusive (refer to FIG. 6 described later).

An optical filter according to the present invention is an optical filter including a multilayer dielectric film,
wherein with respect to ultraviolet light incident at an incidence angle of 0 degrees on the principal surface of the light transmissive window, the optical filter has a band in which the ultraviolet light in a range of wavelengths from 190 nm to 235 nm inclusive is transmitted, and a wavelength $\lambda 5$ at which transmittance of the optical filter indicates 5% is longer than or equal to 236 nm and shorter than 245 nm.

According to the present invention, an improved inactivating device is achieved by suppressing, out of ultraviolet light emitted from the device, an increase in intensity of the ultraviolet light in a wavelength band that affects the human body while increasing intensity of the ultraviolet light in a wavelength band that has a small influence on the human body.

DETAILED DESCRIPTION OF THE PREFERRED EMBODIMENTS

Figure 1:
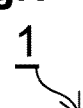
FIG. 1 is a schematic view showing an external appearance of an inactivating device according to an embodiment.
Figure 2:
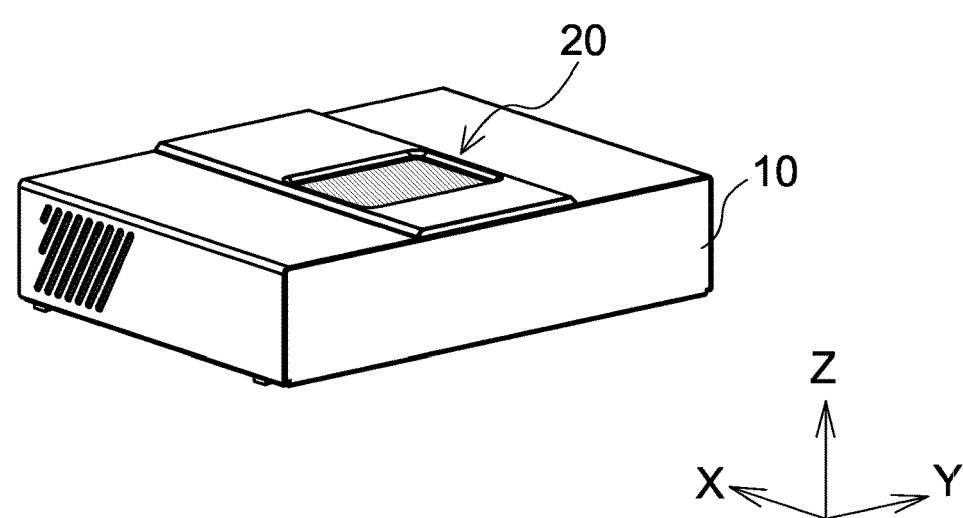
FIG. 2 is a drawing of the inactivating device in FIG. 1, viewed from +Z side.

FIG. 1 is a schematic view showing an external appearance of an inactivating device 1 according to an embodiment, and FIG. 2 is a drawing of the inactivating device 1 in FIG. 1, viewed from +Z side. As shown in FIG. 2, the inactivating device 1 of the present embodiment includes a housing 10 and an ultraviolet light source 30 housed inside the housing 10.

In the description given hereinafter, as shown in FIG. 2, a direction in which a plurality of light-emitting tubes 30a, which are described later and included in the ultraviolet light source 30, are arranged is defined as an X direction. A direction in which the light-emitting tubes 30a are extending is a Y direction, and a direction orthogonal to both the X direction and the Y direction is a Z direction.

In addition, regarding directions, when positive and negative directions are distinguished from each other, each of the directions is indicated with positive or negative sign. That is, the positive direction is indicated as "+Z direction", and the negative direction is indicated as "−Z direction". On the other hand, when the direction is expressed without distinction between positive and negative directions, the direction is simply referred to as "Z direction". For the inactivating device 1 shown in FIGS. 1 and 2, a direction in which ultraviolet light is extracted corresponds to "+Z direction".

As shown in FIGS. 1 and 2, the housing 10 includes a light transmissive window 20 to extract ultraviolet light emitted from the ultraviolet light source 30 out of the housing 10.

Figure 4:
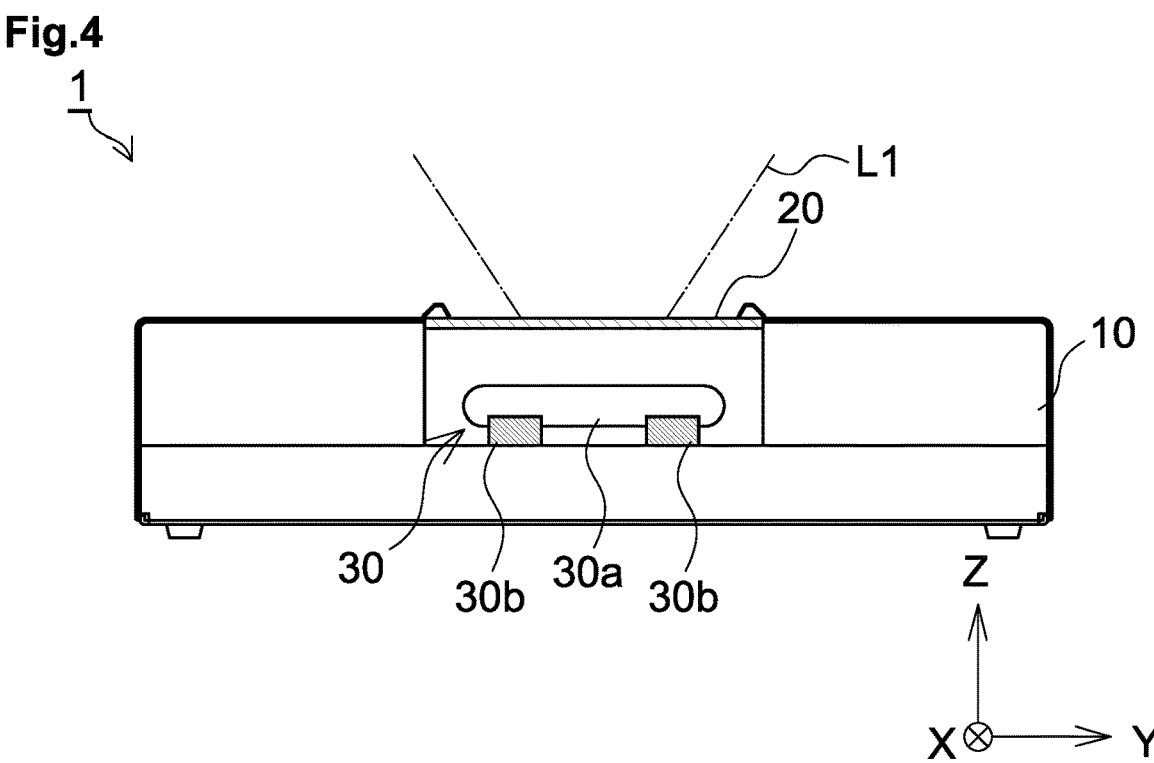
FIG. 4 is a cross-sectional view of the inactivating device of FIG. 1, viewed along an X direction.

In the present embodiment, the ultraviolet light source 30, as shown in FIG. 2, is an excimer lamp that includes the plurality of the light-emitting tubes 30a and a pair of electrodes 30b. As shown in FIG. 4 described later, the plurality of the light-emitting tubes 30a are placed on the pair of the electrodes 30b.

Figure 3:
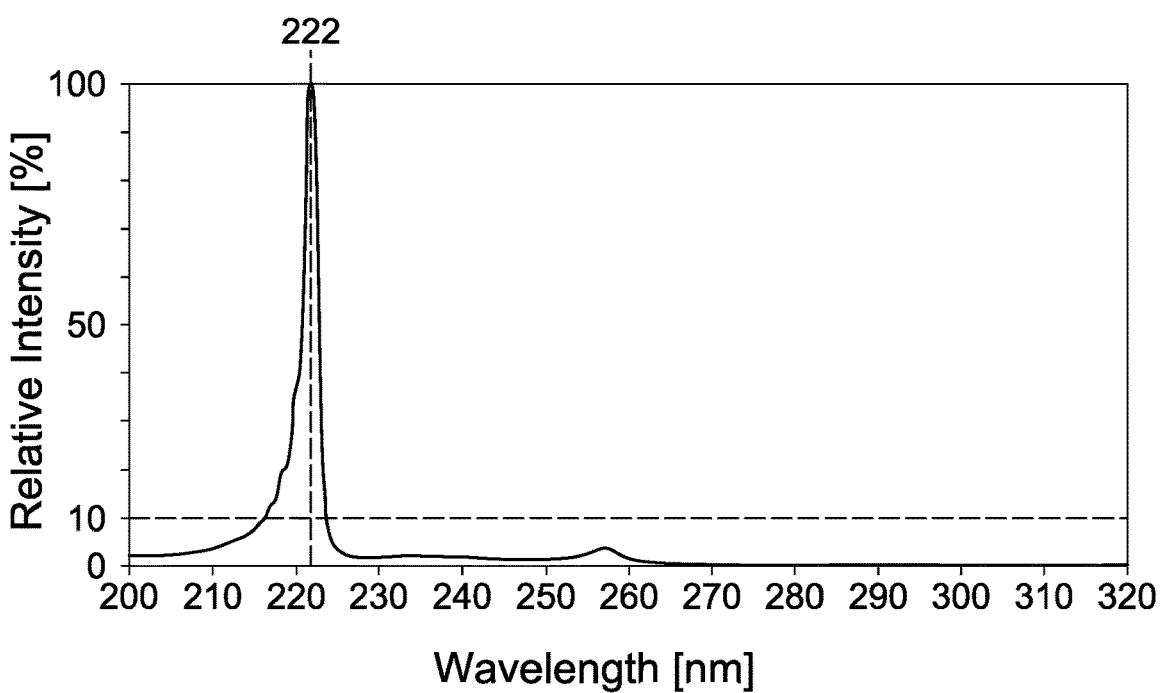
FIG. 3 is a graph showing an example of a spectrum of ultraviolet light generated by an ultraviolet light source.

FIG. 3 is a graph showing an example of a spectrum of ultraviolet light Lx generated by the ultraviolet light source 30. In the present embodiment, krypton (Kr) and chlorine (Cl) as a light-emitting gas G1 are sealed in the light-emitting tubes 30a, and as shown in FIG. 3, the ultraviolet light source 30 emits the ultraviolet light Lx with a peak wavelength of 222 nm when a voltage is applied between the electrodes (30b, 30b). As shown in FIG. 3, the ultraviolet light emitted from the ultraviolet light source 30 exhibits a spectrum that has a main light-emission wavelength band from 216 nm to 223 nm inclusive.

A light source that can be adopted for the ultraviolet light source 30 is one that emits ultraviolet light in a wavelength band in which influence on the human body is small and an inactivating effect is noticed. Thus, the peak wavelength of the emitted ultraviolet light is preferably within a range from 210 nm to 235 nm inclusive and is more preferably within a range from 215 nm to 230 nm inclusive.

Figure 5:
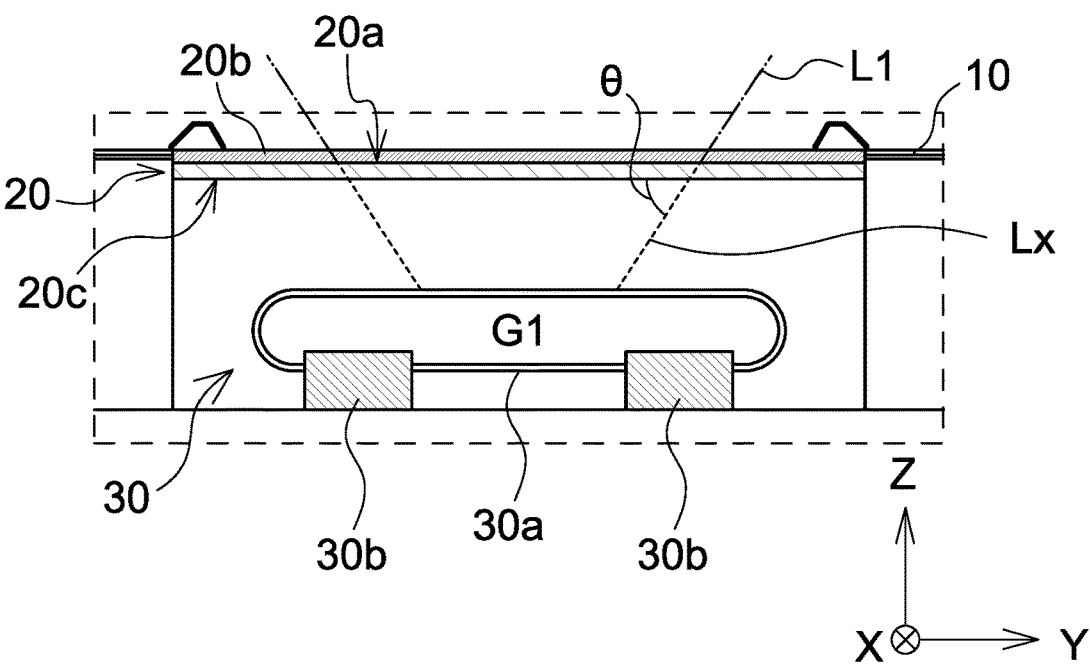
FIG. 5 is an enlarged view of an area around an ultraviolet light source in FIG. 4.

FIG. 4 is a cross-sectional view of the inactivating device 1 of FIG. 1, viewed along the X direction, and FIG. 5 is an enlarged view of an area around the ultraviolet light source 30 in FIG. 4. The light transmissive window 20 is an outgoing light window through which the ultraviolet light emitted from the ultraviolet light source 30 is extracted out of the housing 10. In the present embodiment, an optical filter 20b made from a multilayer dielectric film is formed on a principal surface 20a of the light transmissive window 20.

With the inactivating device 1, ultraviolet light exhibiting the spectrum as shown in FIG. 3 passes through the optical filter 20b, which is described later with reference to FIGS. 4 and 5, and then is extracted to the outside from the light transmissive window 20. In FIGS. 4 and 5, the ultraviolet light that has been generated by the ultraviolet light source 30 is denoted by "ultraviolet light Lx" and the ultraviolet light that has passed through the light transmissive window 20 and that has been extracted out of the inactivating device 1 is denoted by "ultraviolet light L1" to distinguish both states of the ultraviolet light from each other. The similar expressions are used hereinafter as appropriate.

The light transmissive window 20 is made of a material that allows transmission of the ultraviolet light in a wavelength band from 190 nm to 235 nm inclusive. The specific material for the light transmissive window 20 is a ceramic-based material such as silica glass, borosilicate glass, sapphire, magnesium fluoride, calcium fluoride, lithium fluoride and barium fluoride, or a resin-based material such as a silicon resin and a fluororesin, for example, which can be adopted.

The optical filter 20b of the present embodiment is formed, as shown in FIG. 5, on the principal surface 20a of the light transmissive window 20, but may be formed on a principal surface 20c opposed to the principal surface 20a of the light transmissive window 20.

In the present embodiment, a length in a tube-axis direction (the Y direction) of the light-emitting tube 30a of the ultraviolet light source 30 is 70 mm, a distance between the ultraviolet light source 30 and the optical filter 20b is 8 mm, and a size (X, Y) of the optical filter 20b is (60 mm, 45 mm). A configuration of the dimensions described here is merely an example, and the dimensions may have any values with proviso that a relative intensity distribution of the ultraviolet light Lx incident on the optical filter 20b shows an intensity peak at an incidence angle θ from 10 degrees to 50 degrees inclusive.

Figure 6:
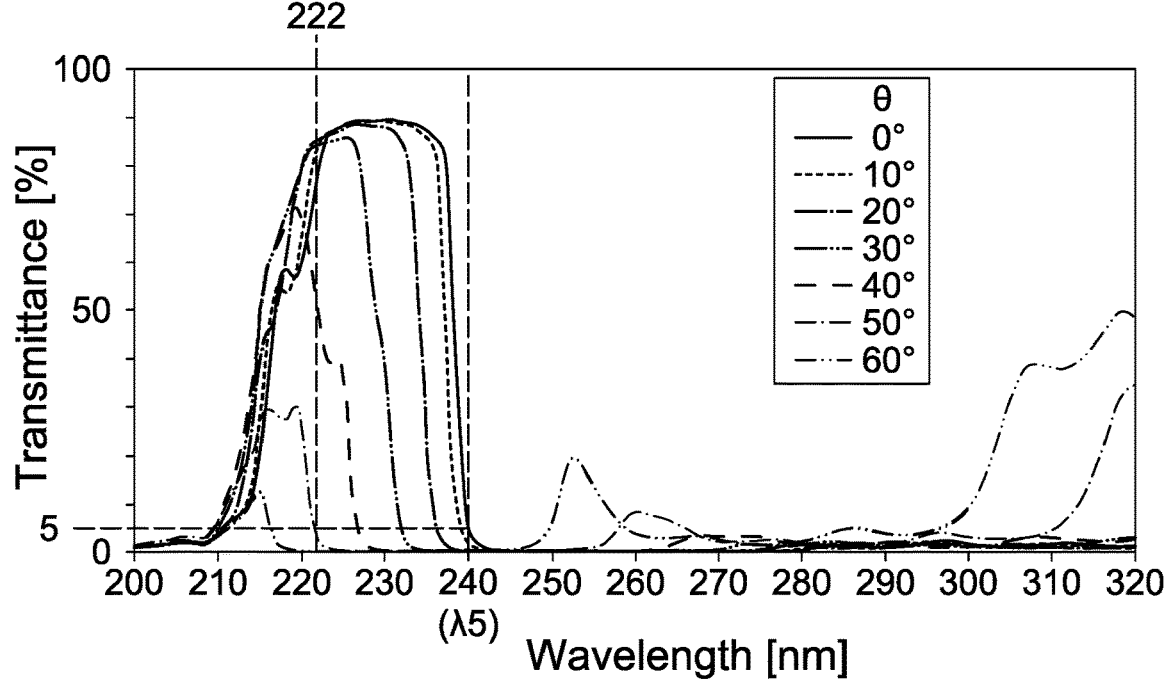
FIG. 6 is a graph showing a transmittance characteristic of an optical filter according to an embodiment by incidence angle θ of ultraviolet light incident on a light transmissive window.

FIG. 6 is a graph showing a transmittance characteristic of the optical filter 20b according to the present embodiment by incidence angle θ of ultraviolet light incident on the principal surface 20a of the light transmissive window 20. In the present embodiment, the optical filter 20b is formed by a multilayer dielectric film and, as shown in FIG. 6, has a band in which the ultraviolet light Lx in a range of wavelengths from 190 nm to 235 nm inclusive is transmitted.

The graph of FIG. 6 is a graph obtained by measuring an optical spectrum of a light beam transmitted through the optical filter 20b using a spectrophotometer. Specifically, FIG. 6 is a graph obtained by changing an outgoing angle corresponding to the incidence angle θ to the optical filter 20b every 10 degrees within a range of 0 degrees to 60 degrees and measuring the transmittance for a wavelength range from 200 nm to 320 nm at each incidence angle θ.

The graph shown in FIG. 6 is produced by superimposing waveforms of the transmittance for the different incidence angles θ on one another, which are obtained by the measurement.

In the present embodiment, the optical filter 20b is configured for ultraviolet light incident at an incidence angle θ of 0 degrees on the principal surface 20a of the light transmissive window 20 such that, as shown in FIG. 6, the wavelength λ5 at which the transmittance indicates 5% is 240 nm (the wavelength λ5 is essentially a wavelength on a long-wavelength side at which the transmittance indicates 5%).

The wavelength λ5 of the optical filter 20b made from a multilayer dielectric film can be adjusted by finely adjusting thicknesses of film layers that make up the multilayer dielectric film.

With an increase in incidence angle θ of the ultraviolet light Lx incident on the light transmissive window 20, the band of the optical filter 20b in which the ultraviolet light Lx is transmitted gradually moves to a short-wavelength side and the peak value of the transmittance gradually goes down. However, in the present embodiment, as shown in FIG. 6, even when the incidence angle θ of the ultraviolet light Lx is more than 40 degrees, the ultraviolet light transmittance of the optical filter 20b maintains 50% or higher at least partially within the wavelength band between 200 nm to 230 nm inclusive.

Figure 7A:
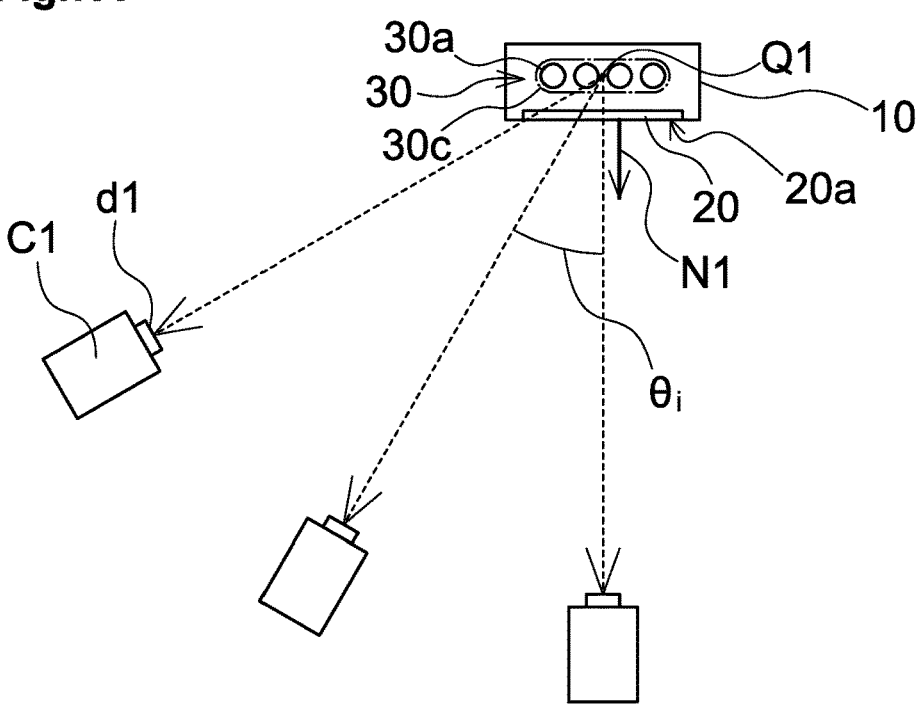
FIG. 7A is a schematic view showing a method for acquiring a relative intensity distribution of ultraviolet light incident on an optical filter formed on a flat surface.
Figure 7B:
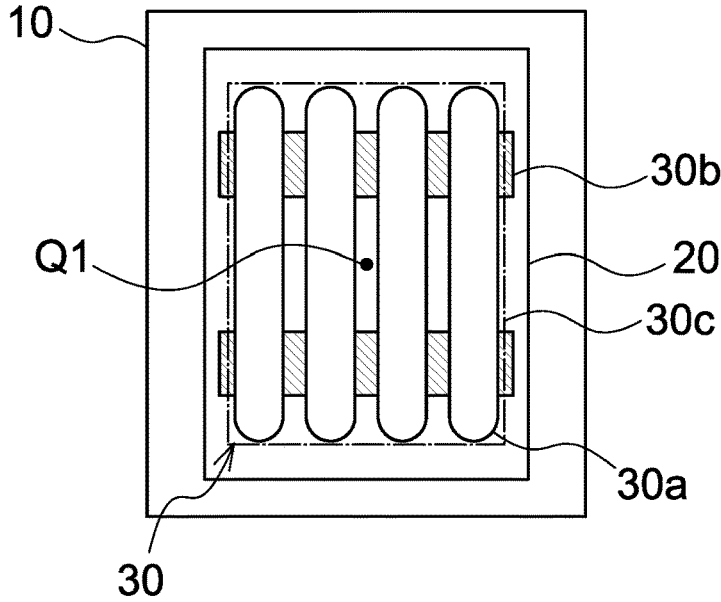
FIG. 7B is a drawing of an ultraviolet light source shown in FIG. 7A, viewed along a direction in which the light is emitted.
Figure 7C:
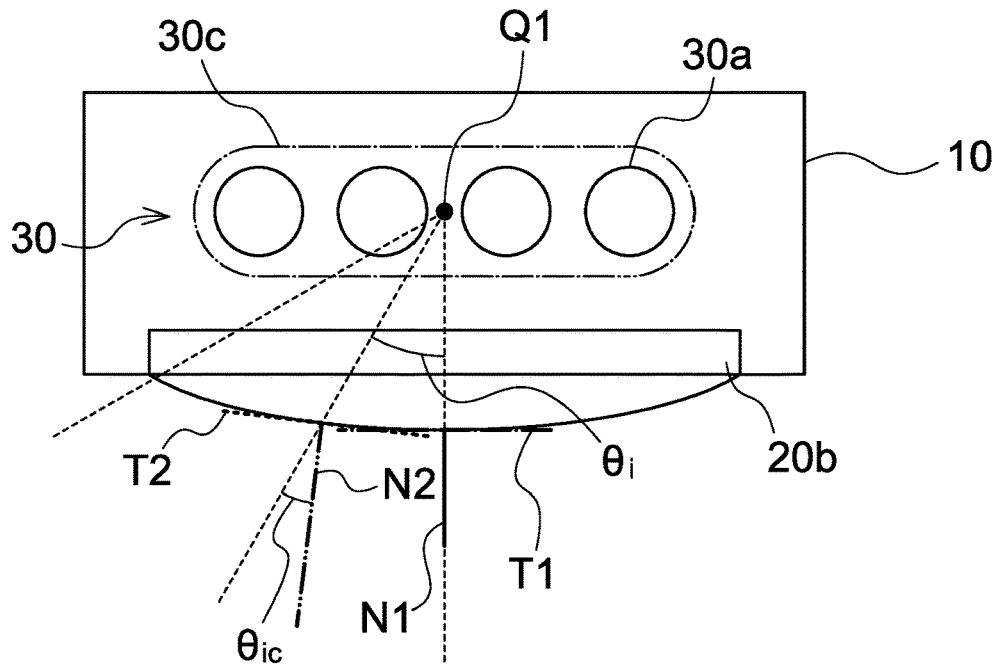
FIG. 7C is a schematic view showing a method for acquiring a relative intensity distribution of ultraviolet light incident on an optical filter formed on a curved surface.

The "relative intensity distribution" in the present specification will now be described with reference to the drawings. FIG. 7A is a schematic view showing a method for acquiring a relative intensity distribution of ultraviolet light incident on the optical filter 20b formed on a flat surface, and FIG. 7B is a drawing of the ultraviolet light source 30 shown in FIG. 7A, viewed along a direction in which the light is emitted. FIG. 7C is a schematic view showing a method for acquiring a relative intensity distribution of ultraviolet light incident on the optical filter 20b formed on a curved surface. The housing 10 that houses the ultraviolet light source 30 shown in FIGS. 7A to 7C is illustrated differently in configuration from the housing 10 illustrated in other drawings for convenience of illustration.

First, the method for acquiring a relative intensity distribution of ultraviolet light incident on the optical filter 20b formed on the principal surface 20a, i.e., a flat surface, of the light transmissive window 20 will be described. For the inactivating device 1 configured without the optical filter 20b as shown in FIGS. 7A and 7B, the intensity of ultraviolet light emitted from the ultraviolet light source 30 is measured by changing an angle θi every 5 degrees in a range of light-emitting angles from 0 degrees to 90 degrees, with respect to a place positioned in a direction of a normal line N1 to the flat surface, on which the optical filter is otherwise formed, from a center Q1 of the ultraviolet light source 30, the place being a place at which the emitted ultraviolet light is detectable, in a first direction (in the present embodiment, a circumferential direction centered on a central axis of a straight line passing through the center Q1 and being parallel to the tube-axis direction of the light-emitting tubes 30a).

The angle θi is defined herein as an angle of the light beam inclined relative to the normal line N1 to the light transmissive window 20, and the light intensity is measured at a place separated at a predetermined distance from the ultraviolet light source 30. As shown in FIG. 7A, for a configuration like the ultraviolet light source 30 that includes the plurality of light-emitting tubes 30a, the light intensity is measured on the assumption that the light is emitted from the center Q1 of a region 30c in which the light-emitting tubes 30a are arranged.

When the light intensity is measured, it is preferred that the distance separated from the ultraviolet light source be 10 times or more of a size of the light source. For instance, in the present embodiment, the separated distance is preferably 50 cm or longer. When the separated distance is satisfactorily ensured, the light source is readily treated as a substantially point source. However, if the separated distance is short, a calculation error is apt to occur.

Next, with the optical filter 20b being removed from the light source, the intensity of the ultraviolet light is measured by changing the angle θi every 5 degrees in a range of light-emitting angles from 0 degrees to ±90 degrees in a second direction (in the present embodiment, a circumferential direction centered on a straight line passing through the center Q1 and being parallel to the direction in which the light-emitting tubes 30a are arranged). The first direction and the second direction are defined, as shown in FIG. 7A, such that routes followed by the place of a measuring instrument C1 moving along measurement points in the respective directions are orthogonal to each other when viewed in the direction of the normal line N1.

By the method described above, a distribution of intensities of the light emitted from the light source without the optical filter 20b is measured at 5-degree intervals in the first direction and the second direction.

Next, using an approach obtained by the method above, light intensities integrated for each component of the angle θi (described herein by circular measure [rad] for convenience of notation) of radiant flux are calculated in view of total luminous flux of the ultraviolet light. Regarding the ultraviolet light incident on the optical filter 20b, when the radiant flux for each component of the angle θi is $V_{\theta i}$, the radiant flux $V_{\theta i}$ is calculated by any of the following equations in mathematical formulas 1 to 3 depending on the value of the angle θi:

$$V_{\theta i} = V_{A\theta i} + V_{B\theta i} = \qquad \text{[Mathematical formula 1]}$$

$$I_{A\theta i}\left\{\pi\left[\cos\theta_i - \cos\left(\theta_i + \frac{\Delta\theta}{2}\right)\right]\right\} + I_{B\theta i}\left\{\pi\left[\cos\theta_i - \cos\left(\theta_i + \frac{\Delta\theta}{2}\right)\right]\right\}$$

The equation in mathematical formula 1 is an equation applied when the angle θi satisfies θi=0.

$$V_{\theta i} = V_{A\theta i} + V_{B\theta i} = \qquad \text{[Mathematical formula 2]}$$

$$I_{A\theta i}\left\{\pi\left[\cos\left(\theta_i - \frac{\Delta\theta}{2}\right) - \cos\left(\theta_i + \frac{\Delta\theta}{2}\right)\right]\right\} + $$
$$I_{B\theta i}\left\{\pi\left[\cos\left(\theta_i - \frac{\Delta\theta}{2}\right) - \cos\left(\theta_i + \frac{\Delta\theta}{2}\right)\right]\right\}$$

The equation in mathematical formula 2 is an equation applied when the angle θi satisfies 0<θi<π.

$$V_{\theta i} = V_{A\theta i} + V_{B\theta i} = \qquad \text{[Mathematical formula 3]}$$

$$I_{A\theta i}\left\{\pi\left[\cos\left(\theta_i - \frac{\Delta\theta}{2}\right) - \cos\theta_i\right]\right\} + I_{B\theta i}\left\{\pi\left[\cos\left(\theta_i - \frac{\Delta\theta}{2}\right) - \cos\theta_i\right]\right\}$$

The equation in mathematical formula 3 is an equation applied when the angle θi satisfies θi=π.

Here, "$I_{A\theta i}$" is the light intensity of the ultraviolet light at the angle θi in the first direction, and "$I_{B\theta i}$" is the light intensity of the ultraviolet light at the angle θi in the second direction. "Δθ" is a measuring angle interval for each of the first direction and the second direction. The measuring angle interval Δθ is π/36 (=5 degrees).

For instance, to calculate the radiant flux $V_{\theta i}$ for an angle component at an angle θi of π/12 (=15 degrees), the light intensity $I_{A\theta i}$ at an ultraviolet light angle θi of 15 degrees in the first direction and the light intensity $I_{B\theta i}$ at an ultraviolet light angle θi of 15 degrees in the second direction are measured. The measuring angle interval Δθ is set to π/36 (=5 degrees). Then, using the equation in mathematical formula 2 applied for an angle θi of π/12 (=15 degrees), the radiant flux Vθi when the angle θi is equal to π/12 (=15 degrees) is calculated.

Figure 7D:
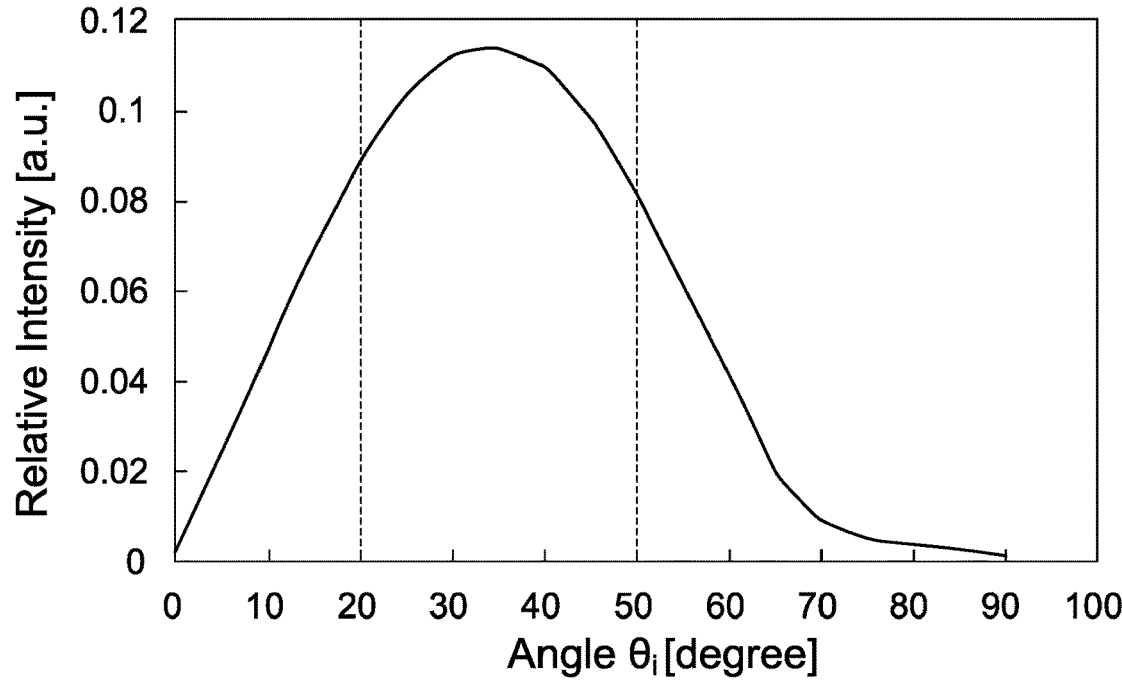
FIG. 7D is a graph showing a relative intensity distribution for a full range of 0 degrees to 90 degrees, the relative intensity distribution relating to radiant flux Vθi for each angle θi of light from an ultraviolet light source with a solid angle being taken into account.

By calculating the radiant flux $V_{\theta i}$ for each angle θi (hereinafter described again by degree measure) through the procedure above and plotting the calculated data on a graph, an angle θi at which the integrated strength shows a peak value can be determined. FIG. 7D is a graph showing a relative intensity distribution for a full range of 0 degrees to 90 degrees, the relative intensity distribution relating to the radiant flux $V_{\theta i}$ for each angle θi in a measuring system shown in FIGS. 7A and 7B. For the ultraviolet light source 30 shown in FIGS. 7A and 7B, a light intensity peak of the radiant flux $V_{\theta i}$ is formed, as shown in FIG. 7D, within a range of the angles θi from 20 degrees to 50 degrees inclusive.

When the optical filter 20b is formed on a curved surface rather than the flat surface, as shown in FIG. 7C, light intensities for each angle θi are measured with respect to the normal line N1 to a contact surface T1. The normal line N1 is a perpendicular drawn from the center Q1 to the contact surface T1.

However, as shown in FIG. 7C, due to a curvature of the optical filter 20b, an angle formed by a travel direction of a light beam subject to measurement with the normal line N1 differs at some places from an angle formed by the light beam travel direction with a normal line N2 to a contact surface T2 at a place through which the light beam is actually passing. Thus, when the optical filter 20b is formed on a curved surface, a correction for the angle θi is made to light intensities of the ultraviolet light radiant flux obtained for each θi. Contents of the correction are described below.

A description will be given here on the assumption that the optical filter 20b is curved, as shown in FIG. 7C, only in the first direction for convenience of description. In a form of the optical filter 20b curved in the first direction, a corrected angle θic for the normal line N2 orthogonal to the contact surface T2 of the optical filter 20b is calculated based on the angle θi between the light emitted from the center Q1 of the ultraviolet light source 30 and the normal line N1.

When the optical filter 20b is formed on the curved surface, the radiant flux $V_{\theta i}$ of ultraviolet light calculated by the method described above is corrected by regarding the radiant flux $V_{\theta i}$ as a light intensity of radiant flux at the corrected angle θic. For instance, while "$V_{A\theta i}$" is radiant flux of the ultraviolet light based on the angle θi in the first direction and "$V_{B\theta i}$" is radiant flux of the ultraviolet light based on the angle θi in the second direction, the radiant flux at the angle θi in the first direction in which the optical filter is curved is regarded as radiant flux at the corrected angle θic and "$V_{A\theta i}$" is treated as radiant flux of the ultraviolet light based on the corrected angle θic.

In this case, by adding a relative intensity distribution amount of the radiant flux "$V_{A\theta i}$" for every corrected angle component in the first direction and a relative intensity distribution amount of the radiant flux "$V_{B\theta i}$" for every angle component without correction in the second direction together, the total relative intensity distribution of the radiant flux "$V_{\theta i}$" after correction is calculated. If the optical filter 20b is also curved in the second direction, light intensities of the radiant flux in the second direction are similarly corrected as described above.

Next, concerning ultraviolet light transmitted through the optical filter 20b and emitted from the housing 10, verification was conducted to ascertain a relationship between the wavelength $\lambda 5$ of the optical filter 20b and the harmful light ratio, and the conducted verification will be described.

The "harmful light ratio" concerning ultraviolet light emitted from the inactivating device is herein defined, as described above, as a ratio of a value of integrated intensities of the ultraviolet light at wavelengths from 235 nm to 320 nm inclusive to a value of integrated intensities of the ultraviolet light at wavelengths from 200 nm to 230 nm inclusive.

As described above, predetermined specification values concerning the integrated irradiation dose of ultraviolet light radiated to the human body are prescribed by wavelength. Hence, the harmful light ratios of inactivating device subject to the verification were compared, with the maximum light intensity value being standardized at "1" such that intensities of the ultraviolet light L1 emitted from the light transmissive windows 20 were equal to each other at the peak wavelength (a wavelength of 222 nm in this verification).

Example 1

In Example 1, the inactivating device 1 described above was used.

Comparative Example 1

Figure 8:
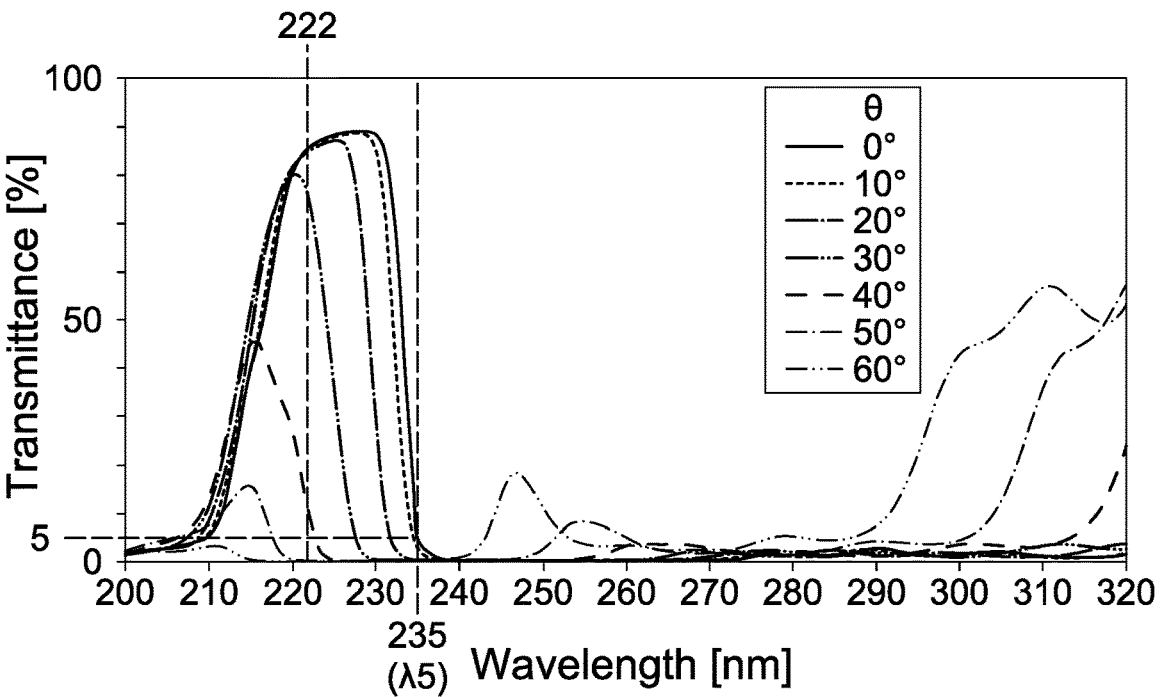
FIG. 8 is a graph showing a transmittance characteristic of an optical filter included in an inactivating device of Comparative Example 1 by incidence angle θ of ultraviolet light incident on a principal surface of a light transmissive window.

In Comparative Example 1, an inactivating device with a configuration common to Example 1 was used except that the wavelength $\lambda 5$ of the optical filter 20b made from a multilayer dielectric film was set to 235 nm by adjusting thicknesses of film layers of the multilayer dielectric film. FIG. 8 is a graph showing a transmittance characteristic of the optical filter included in the inactivating device of Comparative Example 1 by incidence angle $\theta$ of ultraviolet light incident on the light transmissive window 20. The method of producing the graph in FIG. 8 is similar to the case of FIG. 6 described above. It is observed that as compared with the characteristic of the optical filter 20b shown in FIG. 6, a total amount of the ultraviolet light transmitted through the optical filter in Comparative Example 1 is lower in a band of wavelengths from 200 nm to 230 nm inclusive.
(Result)

Figure 9:
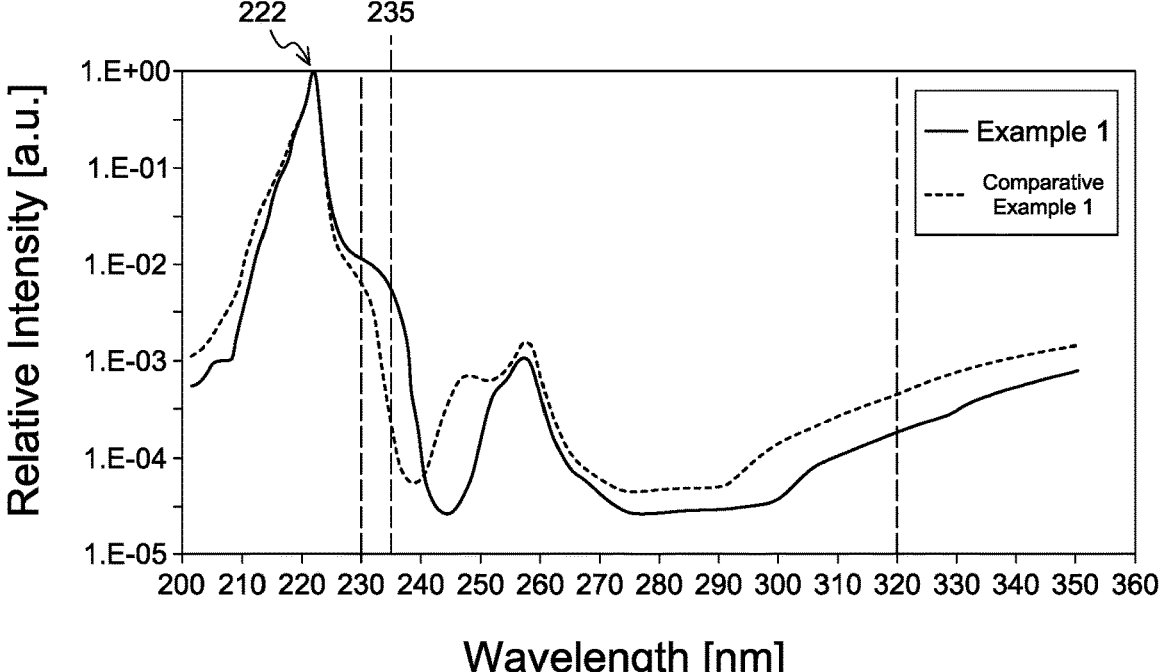
FIG. 9 is a graph obtained by adding up intensities of ultraviolet light emitted from light transmissive windows of inactivating device, respectively, in Example 1 and Comparative Example 1 with a solid angle of the emitted ultraviolet light being taken into account, in consideration of the integrated intensities for each angle component based on relative intensity distributions of radiant flux incident on respective optical filters.

FIG. 9 is a graph obtained by adding up intensities of ultraviolet light emitted from light transmissive windows of the inactivating device, respectively, in Example 1 and Comparative Example 1 with a solid angle of the emitted ultraviolet light being taken into account, in consideration of the integrated intensities for each angle component based on relative intensity distributions of radiant flux incident on the respective optical filters. This is equivalent to a spectrum obtained by homogenizing spectra and relative intensities varying from angle component to angle component in total luminous flux of the ultraviolet light transmitted through the optical filter. In the graph shown in FIG. 9, the vertical axis indicates relative intensities on a logarithmic scale with the light intensity at a wavelength of 222 nm being set to 1. The graph shown in FIG. 9 approximates a spectrum obtained when the light emitted from the optical filter is fully diffused.

The harmful light ratios calculated based on the graph shown in FIG. 9 were 0.69% for Example 1 and 0.72% for Comparative Example 1. In other words, it is observed that the ratio of the intensity of harmful light to the intensity of ultraviolet light used for inactivation is lower for the ultraviolet light L1 emitted from the inactivating device 1 in Example 1 compared with the ultraviolet light emitted from the inactivating device in Comparative Example 1.

As for the optical filter 20b of Example 1, the transmittance for the incidence angle $\theta$ of 60 degrees, as shown in FIG. 6, starts to rise in a neighborhood of the 300 nm wavelength, and the transmittance for the incidence angle $\theta$ of 50 degrees starts rise in a neighborhood of the 310 nm wavelength. In contract to this, as for the optical filter of Comparative Example 1, the transmittance for the incidence angle $\theta$ of 60 degrees, as shown in FIG. 8, starts to rise in a neighborhood of the 290 nm wavelength, the transmittance for the incidence angle $\theta$ of 50 degrees starts to rise in a neighborhood of the 300 nm wavelength, and the transmittance for the incidence angle $\theta$ of 40 degrees starts to rise in a neighborhood of the 310 nm wavelength.

When the wavelength $\lambda 5$ of the optical filter made from a multilayer dielectric film is changed by adjusting thicknesses of film layers of the multilayer dielectric film, the transmittance characteristic changes in response to a change in wavelength $\lambda 5$. Specifically, as shown in FIGS. 6 and 8, in response to a change in wavelength $\lambda 5$ to the short-wavelength side, the band present in the neighborhood of the 300 nm wavelength in which the transmittance starts to rise moves to the short-wavelength side.

As a result of this, as in the graph shown in FIG. 9, the relative intensity of the ultraviolet light in Comparative Example 1 is higher than the intensity of the ultraviolet light L1 in Example 1 at wavelengths from 240 nm to 320 nm.

Further, as shown in FIGS. 6 and 8, for any of the optical filters, the transmittance is less than or equal to 10% in a band of wavelengths from 200 nm to 210 nm, and the transmittance rises with an increase in wavelength from 210 nm to the long-wavelength side. The characteristic changes little in response to a change in wavelength $\lambda 5$. This is because whereas the wavelength range in which the ultraviolet light is obstructed is changed by optical filter film design on the long-wavelength side, the ultraviolet light on the short-wavelength side is absorbed by the optical filter.

As described above, the light intensity of the ultraviolet light Lx generated by the ultraviolet light source 30 is adjusted such that an integrated light amount of the ultraviolet light L1, which is emitted from the light transmissive window 20, at the peak wavelength (in this verification, a wavelength of 222 nm) is a predetermined specification value (in this verification, 22 mJ/cm²). In this case, the transmittance at the peak wavelength for the ultraviolet light source 30 in Example 1 is readily maintained at a high level compared with the ultraviolet light source 30 in Comparative Example 1. Thus, it is observed that when the ultraviolet light is radiated until the integrated light amount of the peak wavelength reaches the predetermined specification value, the harmful light ratio of the ultraviolet light source 30 in Example 1 does not deteriorate and is low in FIG. 9 compared with the ultraviolet light source 30 in Comparative Example 1.

As a result, the integrated light intensity value of the inactivating device 1 in Example 1 changes only slightly in the band of wavelengths from 200 nm to 230 nm inclusive and changes in a direction to a lower level in the band of wavelengths from 235 nm to 320 nm inclusive compared with the inactivating device in Comparative Example 1.

Figure 10:
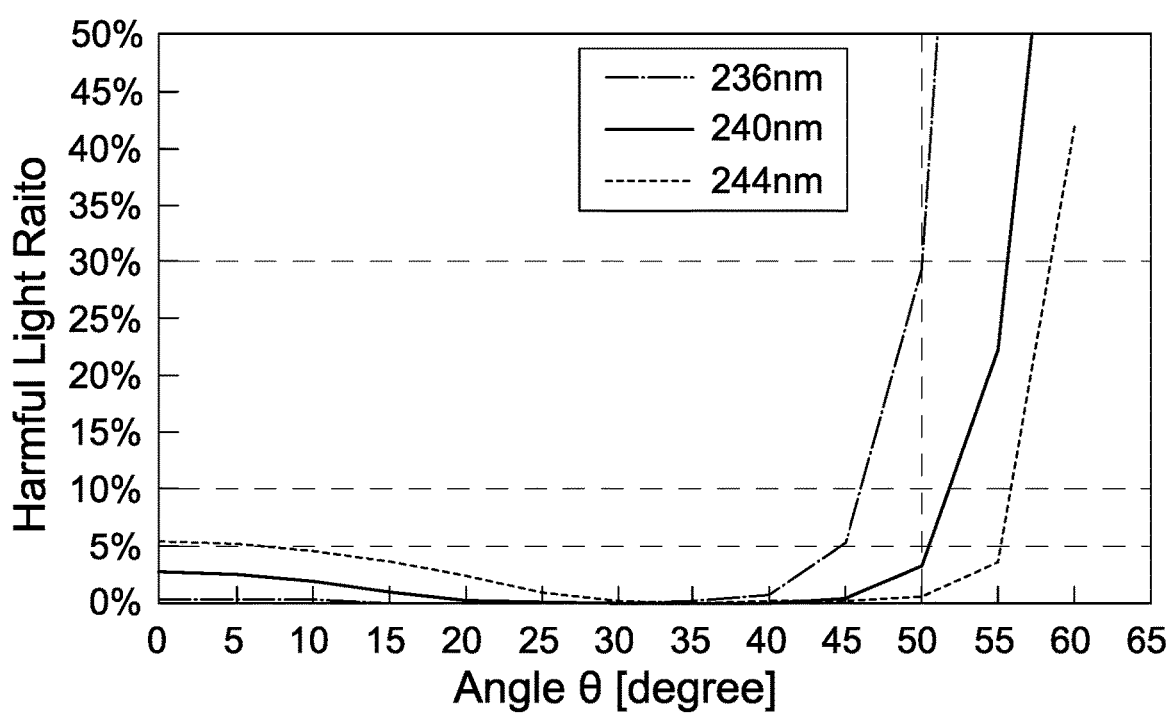
FIG. 10 is a graph showing a harmful light ratio of an optical filter by incidence angle θ.

FIG. 10 is a graph showing the harmful light ratio of the optical filter 20b by incidence angle $\theta$. The vertical axis indicates the harmful light ratio and the horizontal axis indicates the incidence angle $\theta$. As shown in FIG. 10, for the optical filter designed such that the wavelength $\lambda 5$ is 236 nm, the harmful light ratio is less than or equal to 30% when the incidence angle θ is in a range of 0 degrees to 50 degrees, and the harmful light ratio is higher than 30% when the incidence angle θ is greater than or equal to 50 degrees.

For the optical filter designed such that the wavelength λ5 is 244 nm, the harmful light ratio is more than 5.0% when the incidence angle θ is 0 degrees and gradually decreases with an increase in incidence angle θ. The harmful light ratio is less than or equal to 5.0% when the incidence angle θ is in a range of 10 degrees to 50 degrees. The harmful light ratio is more than 30% when the incidence angle θ is greater than 60 degrees.

The findings described above reveal that the incidence angle θ at which the intensity shows a peak in the relative intensity distribution is preferably included in a range from 10 degrees to 50 degrees inclusive to ensure that the peak value of radiant flux for every angle component of the ultraviolet light incident on the optical filter is disposed at least in a range in which the harmful light ratio is reduced to less than or equal to 30%. It is also observed that to reduce the harmful light ratio further, the incidence angle θ at which the intensity shows a peak in the relative intensity distribution is more preferably included in a range from 10 degrees to 45 degrees inclusive and is particularly preferably included in a range from 20 degrees to 40 degrees inclusive.

Figure 11:
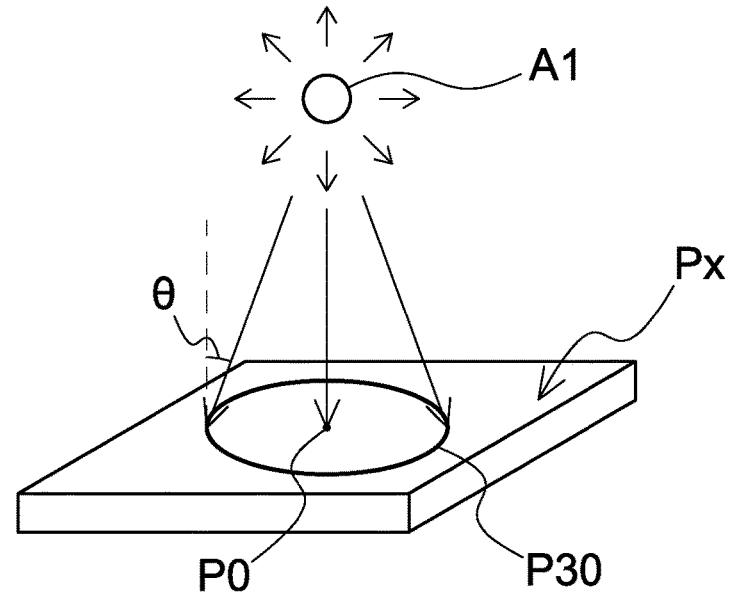
FIG. 11 is a drawing illustrating traveling of beams of light uniformly emitted from a point source in all directions.

Lastly, a description will be given to prove that the relative intensity distribution of the ultraviolet light Lx incident on the optical filter 20b in the present embodiment shows an intensity peak at the incidence angle θ ranging from 20 degrees to 50 degrees inclusive. FIG. 11 is a drawing illustrating traveling of beams of light uniformly emitted from a point source A1 in all directions. Let us assume that as shown in FIG. 11, uniform beams of light are emitted from the point source A1 in all directions, and a flat surface Px is irradiated with part of the light.

As shown in FIG. 11, in the flat surface Px, a region on which the light beams emitted from the point source A1 are incident at the incidence angle θ of 0 degrees is P0, and a region on which the light beams are incident at the incidence angle θ of 30 degrees is P30. In the flat surface Px, as observed from FIG. 11, whereas the region P0 is only one point, the region P30 is an annular region centered on the region P0.

Moreover, as described above, it is observed that when uniform beams of light are emitted from the point source A1 in all directions, a total of the light beams incident on the overall region P30 forming an annular region are greater than the light beams incident only on one point of the region P0. In other words, assuming that the light source is a point source, a gross amount of the light beams incident on a predetermined surface increases with an increase in incidence angle θ from 0 degrees. This means that the relative intensity of radiant flux for each angle component is measured higher in the region P30 than in the region P0.

The ultraviolet light source 30 included in the inactivating device 1 of the present embodiment can be regarded as an equivalent in which point sources are arranged in the tube-axis direction of the light-emitting tubes 30a. Then, assuming that each of the arranged point sources is considered, the beams incident on the optical filter 20b are minimum when the incidence angle θ is 0 degrees. With an increase in incidence angle θ from 0 degrees, the gross amount of the beams gradually increases.

The intensity of the ultraviolet light Lx incident on the optical filter 20b is proportional to the amount of the beams. The amount of the beams incident on the optical filter 20b increases with an increase in incidence angle θ from 0 degrees. Once the incidence angle θ gets somewhat larger, the amount of beams that cannot be incident on the optical filter 20b increases and thus the amount of beams of the ultraviolet light Lx decreases. The incidence angle θ at which the amount of the incident beams starts decreasing is adjusted by the distance between the ultraviolet light source 30 and the optical filter 20b, a size of the light-emitting tube 30a of the ultraviolet light source 30, an area formed by the optical filter 20b, and other factors. Specific sizes of the ultraviolet light source 30 and the optical filter 20b, and other dimensions are as described above.

The results above prove that the optical filter 20b configured such that the wavelength λ5 is longer than or equal to 236 nm and shorter than 245 nm has a relatively high effect on reduction of the harmful light ratio for the ultraviolet light Lx incident at the incidence angle θ ranging from 10 degrees to 50 degrees. Thus, it is preferred that in the relative intensity distribution of the ultraviolet light Lx incident on the optical filter 20b, the light intensity outside a range of the incidence angle θ from 10 degrees to 50 degrees is lower than the light intensity in a range of the incidence angle θ from 10 degrees to 50 degrees. In other words, it is preferred that the relative intensity distribution of the ultraviolet light Lx incident on the optical filter 20b shows an intensity peak at the incidence angle θ in a range from 10 degrees to 50 degrees.

For the reason described above, the ultraviolet light L1 emitted from the inactivating device 1 in Example 1 gave the result of a low harmful light ratio compared with the ultraviolet light emitted from the inactivating device in comparative Example 1.

Thus, the inactivating device 1 configured as described above is able to reduce the ratio of ultraviolet light affecting the human body, which is contained in the emitted ultraviolet light L1. In other words, it is possible to achieve the inactivating device 1, which reduces intensity of ultraviolet light in a wavelength band that affects the human body to a level equal to or lower than the conventional intensity level while increasing intensity of the ultraviolet light in a wavelength band that has a small influence on the human body.

As shown in FIG. 9, in Example 1 as compared to Comparative Example 1, the amount of the ultraviolet light is relatively high at wavelengths from 235 nm to 240 nm and is relatively low at wavelengths from 240 nm to 320 nm. In other words, the amount of the ultraviolet light in the 240 nm to 280 nm wavelength band, which has a more substantial influence on the human body, is reduced further, and the amount of the ultraviolet light at wavelengths from 235 nm to 240 nm, which are satisfactorily safe compared with the other wavelength band, is increased. Hence, it is thought that in Example 1, within the band of wavelengths from 235 nm to 320 nm inclusive, including a wavelength range with a potential influence on the human body, the light intensity in a wavelength zone with a substantial influence on the human body is further reduced, and safety is further improved.

As described above, to lower the harmful light ratio, it is preferable to lower the integrated value of light intensity in the band of wavelengths from 235 nm to 320 nm inclusive while suppressing a decrease in integrated value of light intensity in the band of wavelengths from 200 nm to 230 nm inclusive.

Thus, the optical filter is preferably a low-pass filter that limits at least partly transmission of the ultraviolet light in the wavelength range from 235 nm to 320 nm inclusive. This reduces the occurrence of a decrease in integrated value of light intensity in the band of wavelengths from 200 nm to 230 nm inclusive.

The optical filter may be a bandpass filter that limits at least partly transmission of the ultraviolet light in a band of wavelengths from 235 nm to 320 nm inclusive while allowing transmission of the ultraviolet light at wavelengths from 200 nm to 230 nm inclusive. In this case, it is preferred that the optical filter is formed by a member that includes a material to absorb the ultraviolet light in a wavelength range of shorter than or equal to 200 nm. Even if an end of the band at which the ultraviolet light is absorbed is changed by optical filter film design, the optical filter absorbs the ultraviolet light in a range of shorter than or equal to 200 nm. This stably limits transmission of the ultraviolet light in a wavelength range of shorter than or equal to 200 nm and readily stabilizes the light intensity in a band of wavelengths from 200 nm to 230 nm inclusive. Examples of the material that absorbs the ultraviolet light in a wavelength range of shorter than or equal to 200 nm include $HfO_2$ and $Y_2O_3$.

As described above, the optical filter 20b is an optical filter designed such that the wavelength λ5, at which the transmittance indicates 5%, is longer than or equal to 236 nm and shorter than 245 nm. This helps to lower the harmful light ratio. If the optical filter is a low-pass filter that has the wavelength λ5 of longer than or equal to 236 nm and shorter than 245 nm and that allows transmission of the ultraviolet light at wavelengths from 200 nm to 230 nm, this is likely to prevent a difference in optical filter film design from causing the transmittance to deteriorate for the ultraviolet light in a wavelength range of shorter than or equal to 230 nm. In addition, if the optical filter is a bandpass filter made of a material that absorbs the ultraviolet light in a wavelength range of shorter than or equal to 200 nm, this stably limits transmission of the ultraviolet light in a wavelength range of shorter than or equal to 200 nm and readily stabilizes the intensity of the ultraviolet light at wavelengths from 200 nm to 230 nm inclusive.

In the present embodiment, the optical filter 20b is configured such that the wavelength λ5 is 240 nm. However, according to the verification results, it is preferred that the wavelength λ5 of the optical filter 20b is longer than or equal to 236 nm and shorter than 245 nm from the viewpoint of reducing the amount of ultraviolet right that is in a wavelength band affecting the human body and that is extracted from the housing 10. To further reduce the amount of ultraviolet right that is in a wavelength band affecting the human body and that is extracted from the housing 10, an upper wavelength limit on the wavelength λ5 of the optical filter 20b is preferably shorter than or equal to 243 nm and is more preferably shorter than or equal to 242 nm. In addition, to further increase the intensity of the ultraviolet light in a wavelength band with a small influence on the human body, a lower wavelength limit on the wavelength λ5 of the optical filter 20b is preferably longer than or equal to 237 nm, is preferably longer than or equal to 238 nm, and is more preferably longer than or equal to 239 nm. Based on the figures above, the wavelength λ5 of the optical filter is more preferably, for example, from 238 nm to 243 nm inclusive.

In the present embodiment, the ultraviolet light source 30 may be a light source that generates the ultraviolet light Lx, a main light-emission wavelength band of which is at least partly included in a range from 200 nm to 230 nm inclusive. The ultraviolet light source 30 may, for example, be an excimer lamp that includes the light-emitting tubes 30a in which krypton (Kr) gas and bromine (Br) gas as a light-emitting gas G1 are sealed and that emits the ultraviolet light Lx with a peak wavelength of 207 nm. The ultraviolet light source may be a light source that includes either an LED (light-emitting diode), an LD (laser diode), or a wavelength converter and that has a peak wavelength within a range from 200 nm to 235 nm inclusive.

OTHER EMBODIMENTS

Other embodiments will be described.

Figure 12:
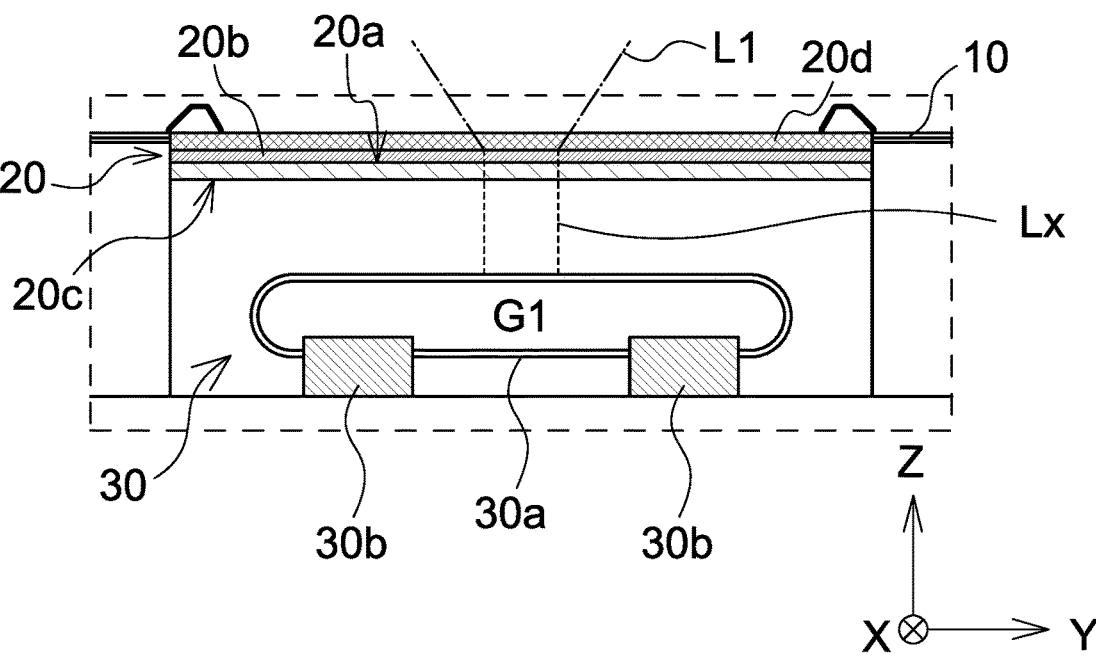
FIG. 12 is an enlarged view of an area around an ultraviolet light source in an inactivating device according to another embodiment.

<1> FIG. 12 is an enlarged view of an area around the ultraviolet light source 30 in the inactivating device 1 according to another embodiment. As shown in FIG. 12, the inactivating device 1 may further include a diffusion member 20d downstream of the optical filter 20b to diffuse ultraviolet light L1 emitted from the optical filter 20b.

The diffusion member 20d diffuses the ultraviolet light L1 transmitted through the optical filter 20b to homogenize light intensities, spectra, and other properties of the ultraviolet light L1 that vary from angle component to angle component, the ultraviolet light L1 being emitted from the optical filter 20b. As a result, beams of the ultraviolet light L1 emitted from the inactivating device 1 are rendered into beams that each have a characteristic substantially identical to that of the spectrum shown in FIG. 9. This configuration allows the inactivating device 1 to increase intensity of the ultraviolet light in a wavelength band that has a small influence on the human body, irradiate a wider area with the ultraviolet light L1 at a kept or reduced harmful light ratio, and inactivate bacteria or viruses in the wider area efficiently and with improved safety.

In the present embodiment, as shown in FIG. 12, the diffusion member 20d is directly placed on top of the optical filter 20b of the light transmissive window 20 in the illustrated configuration. However, the configuration for the diffusion member 20d is not limited to this configuration. For instance, the diffusion member 20d may be fastened to the housing 10 with another member of screws, or may be disposed separately from the optical filter 20b.

Figure 13:
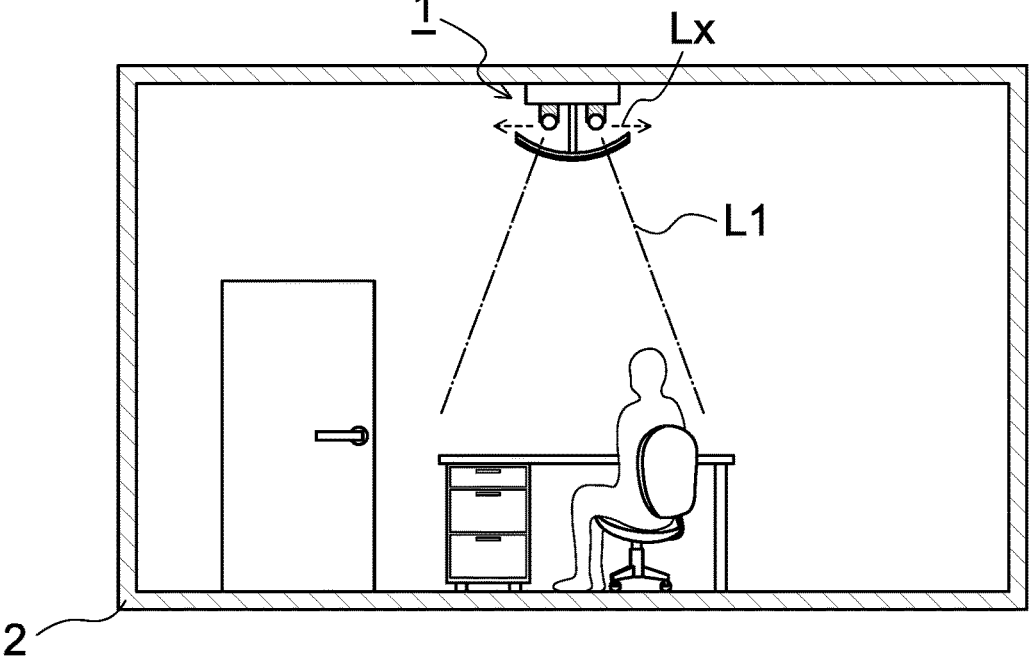
FIG. 13 is a schematic view showing an example of an implementation mode of an inactivating device according to another embodiment.
Figure 14:
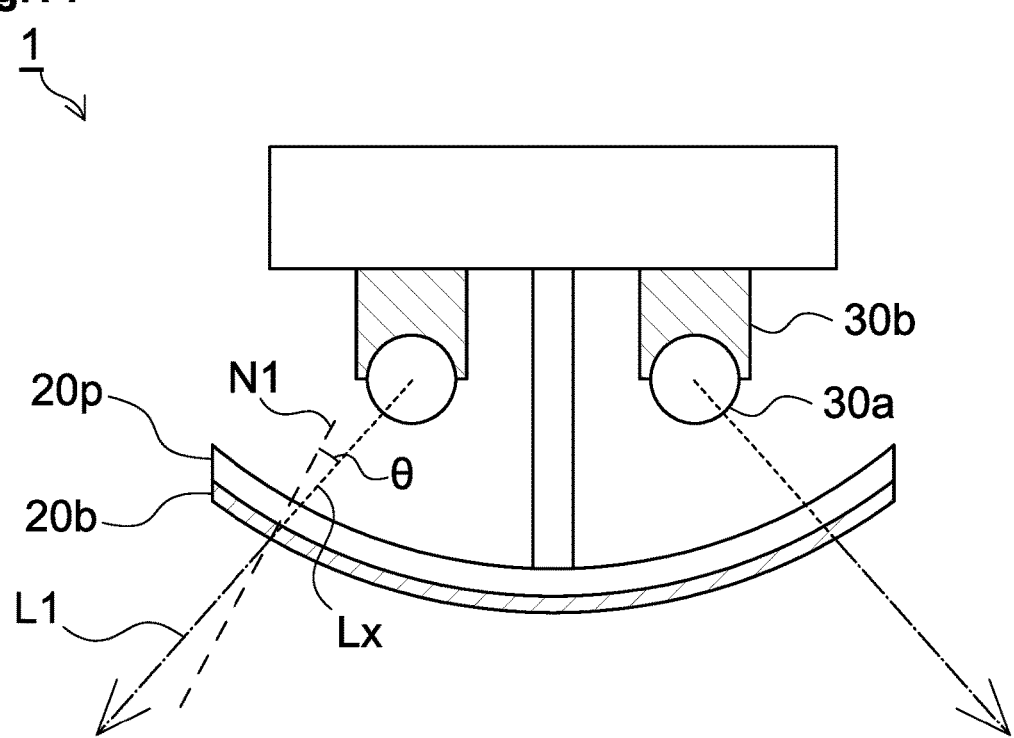
FIG. 14 is an enlarged view of the inactivating device in FIG. 13.

<2> FIG. 13 is a schematic view showing an example of an implementation mode of the inactivating device 1 according to another embodiment. FIG. 14 is an enlarged view of the inactivating device 1 in FIG. 13. As shown in FIG. 14, a configuration of the inactivating device 1 may include the optical filter 20b that is formed on a plate 20p disposed simply on a part of a periphery of the ultraviolet light source 30 without the housing 10.

The material that the light transmissive window 20 is made of may be adopted for a material for the plate 20p. As shown in FIG. 14, the plate 20p is formed in a curved shape, but may be formed in a flat shape.

In the present embodiment, as shown in FIG. 14, the plate 20p is formed in a curved shape, and thus the optical filter 20b is formed on a curved surface rather than a flat surface. In such a case, a distribution of a relative intensity for each angle component of radiant flux of the ultraviolet light Lx incident on the optical filter 20b is measured, as shown in FIG. 14, for every angle (incidence angle θ) inclined at each predetermined place relative to the normal line N1 by the measuring method described with reference to FIGS. 7A and 7B.

As shown in FIG. 13, by the inactivating device configured as described above, a lower space of a room 2 where people are coming and going is irradiated, for example, with the ultraviolet light L1 at a reduced harmful light ratio. An upper space of the room 2 that is above a height of people is irradiated with the ultraviolet light Lx, which is left untouched and is not attenuated by the plate 20p and the optical filter 20b. An aerosol and other substances that are present in the room 2 and subject to inactivation circulate through the lower space and the upper space inside the room 2 by natural convection. Thus, the upper space of the room 2 is irradiated with the high-intensity ultraviolet light Lx and thereby inactivation of bacteria or viruses inside the room 2 makes progress by natural convection.

Thus, the inactivating device 1 of the present embodiment can achieve both safety for people and highly efficient inactivation.

Figure 15:
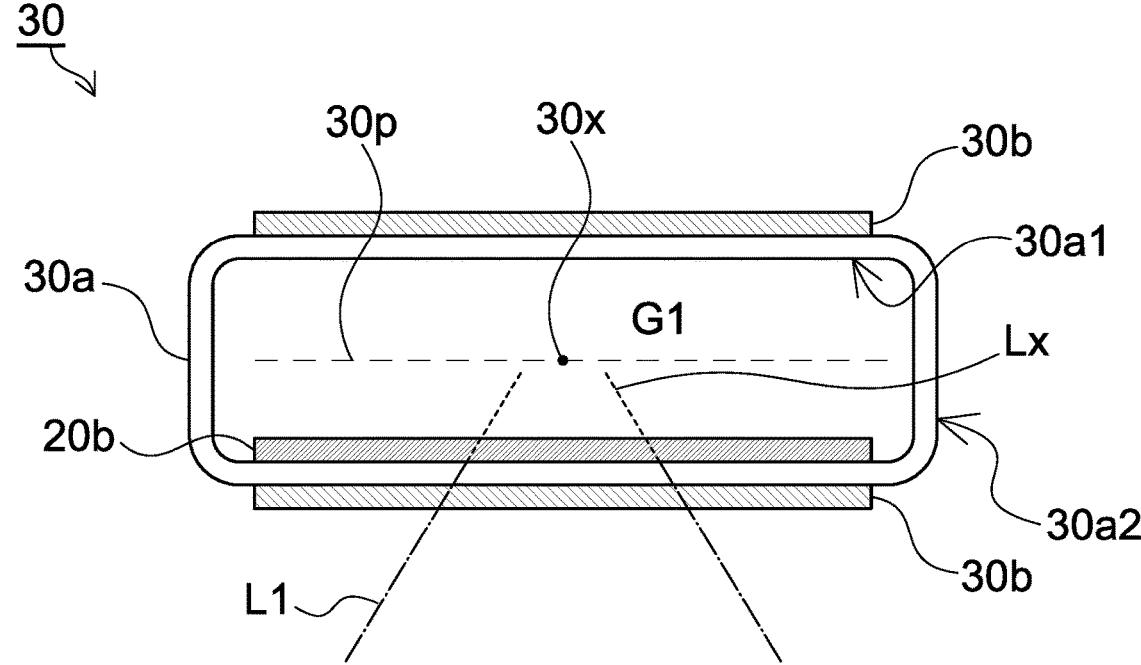
FIG. 15 is a schematic view showing a configuration of an ultraviolet light source in an inactivating device according to another embodiment.

<3> FIG. 15 is a schematic view showing a configuration of the ultraviolet light source 30 in the inactivating device 1 according to another embodiment. In the inactivating device 1, the optical filter 20*b* may, as shown in FIG. 15, be formed on a wall surface of the light-emitting tube 30*a*, a component of the ultraviolet light source 30, with proviso that the ultraviolet light source is configured such that the relative intensity distribution of ultraviolet light Lx incident on the optical filter 20*b* has an intensity peak in a range of the incidence angle from 20 degrees to 50 degrees inclusive. A place on which the optical filter 20*b* is formed may be an inner wall surface 30*al* or an outer wall surface 30*a*2 of the light-emitting tube 30*a*.

The ultraviolet light source 30 shown in FIG. 15 is an excimer lamp having what is called a flat tube shape. A cross section of the excimer lamp cut along a tube axis 30*x* has a rectangular shape. The pair of electrodes (30*b*, 30*b*) are disposed opposite to each other through the light-emitting tube 30*a* in which a light-emitting gas G1 is sealed. When a voltage is applied between the electrodes, the ultraviolet light Lx is generated inside the light-emitting tube 30*a*. At this time, the ultraviolet light Lx is generated most in a vicinity of a flat surface 30*p* that is parallel to the electrodes (30*b*, 30*b*) and that includes the tube axis 30*x*.

An example of an approximate calculation of a relative intensity distribution of the ultraviolet light Lx incident on the optical filter 20*b* in the present embodiment will now be described. First, let us assume that a plurality of point sources are densely arranged on the flat surface 30*p* to emit identical beams of light in all directions. Then, when light emitted from each of the point sources is viewed from the optical filter 20*b*, the beams incident at 0 degrees is the smallest in volume and the beams increase with an increase in angle. The beams coming in at an incidence angle wider than or equal to a certain-degree angle are not incident on the optical filter 20*b*.

In other words, when the amount of the ultraviolet light Lx incident on the optical filter 20*b* is adjusted by adjusting properties of the flat tube-shaped excimer lamp, such as a distance between the electrodes (30*b*, 30*b*) and a width of the light-emitting tube 30*a* (a distance between opposing wall surfaces in a direction orthogonal to both the direction of the tube axis 30*x* and a direction in which the electrodes (30*b*, 30*b*) are opposed to each other), the ultraviolet light Lx incident on the optical filter 20*b* shows a relative intensity distribution that includes a peak intensity at an incidence angle θ from 20 degrees to 50 degrees inclusive.

An example of a specific size of the ultraviolet light source 30 included in the flat tube-shaped excimer lamp, which can be adopted for the inactivating device 1, is given. The distance between the electrodes (30*b*, 30*b*) is 8 mm, the width of the light-emitting tube 30*a* is 20 mm, and a length of the light-emitting tube 30*a* along the tube axis 30*x* is 100 mm. The optical filter 20*b* is formed on an overall flat area of the inner wall surface 30*a*1 or the outer wall surface 30*a*2.

The configuration described above is merely an example. With proviso that the relative intensity distribution satisfies a predetermined condition, the ultraviolet light source 30 may be an excimer lamp in any shape, such as an excimer lamp that has a double-tube shape, other than the flat tube shape. An LED, a laser, or other devices may be used as a light source other than the excimer lamp.

<4> The configurations of the inactivating device 1 described above are merely examples, and the present invention is not limited to the illustrated configurations.

What is claimed is:

1. An inactivating device comprising:

an ultraviolet light source to emit ultraviolet light, a main light-emission wavelength band of the ultraviolet light being at least partly included in a range from 200 nm to 230 nm inclusive; and an optical filter including a multilayer dielectric film, the ultraviolet light generated by the ultraviolet light source being incident on the optical filter, wherein with respect to the ultraviolet light incident at an incidence angle of 0 degrees, the optical filter:

has a band in which the ultraviolet light in a range of wavelengths from 190 nm to 235 nm inclusive is transmitted, has a transmittance greater than 5% at a wavelength of 235 nm, and has a wavelength $\lambda 5$ that is longer than or equal to 237 nm and shorter than 245 nm, wherein the wavelength $\lambda 5$ is defined as a wavelength at which the transmittance of the optical filter is 5%, and wherein in a distribution of a relative intensity for each angle component of radiant flux of the ultraviolet light generated by the ultraviolet light source and incident on the optical filter, the incidence angle at which the relative intensity shows a peak value is included in a range from 10 degrees to 50 degrees inclusive.

2. The inactivating device according to claim 1, further comprising:

a housing that houses the ultraviolet light source; and a light transmissive window to extract the ultraviolet light out of the housing, wherein the optical filter is disposed on a principal surface of the light transmissive window.

3. The inactivating device according to claim 1, wherein the wavelength $\lambda 5$ of the optical filter is longer than or equal to 238 nm and shorter than 243 nm.

4. The inactivating device according to claim 1, wherein the optical filter includes a member that includes a material to absorb the ultraviolet light in a wavelength range of shorter than or equal to 200 nm.

5. The inactivating device according to claim 1, wherein the ultraviolet light source emits the ultraviolet light that has a peak wavelength within a range from 210 nm to 235 nm inclusive.

6. The inactivating device according to claim 1, wherein the ultraviolet light source is an excimer lamp that includes a light-emitting tube in which a gas containing krypton (Kr) and chlorine (Cl) as a light-emitting gas is sealed.

7. An optical filter included in an inactivating device, the inactivating device comprising an ultraviolet light source to emit ultraviolet light, a main light-emission wavelength band of the ultraviolet light being at least partly included in a range from 200 nm to 230 nm inclusive, the optical filter including:

a multilayer dielectric film, the ultraviolet light generated by the ultraviolet light source being incident on the optical filter, wherein with respect to ultraviolet light incident at an incidence angle of 0 degrees on the optical filter, the optical filter:

has a band in which the ultraviolet light in a range of
wavelengths from 190 nm to 235 nm inclusive is
transmitted, has a transmittance greater than 5% at a wavelength of
235 nm, and has a wavelength $\lambda 5$ that is longer than or equal to 237 nm
and shorter than 245 nm, wherein the wavelength $\lambda 5$ is defined as a wavelength at
which the transmittance of the optical filter is 5%, and wherein in a distribution of a relative intensity for each
angle component of radiant flux of the ultraviolet light
generated by the ultraviolet light source and incident on
the optical filter, the incidence angle at which the
relative intensity shows a peak value is included in a
range from 10 degrees to 50 degrees inclusive.

* * * * *